Figure 1:
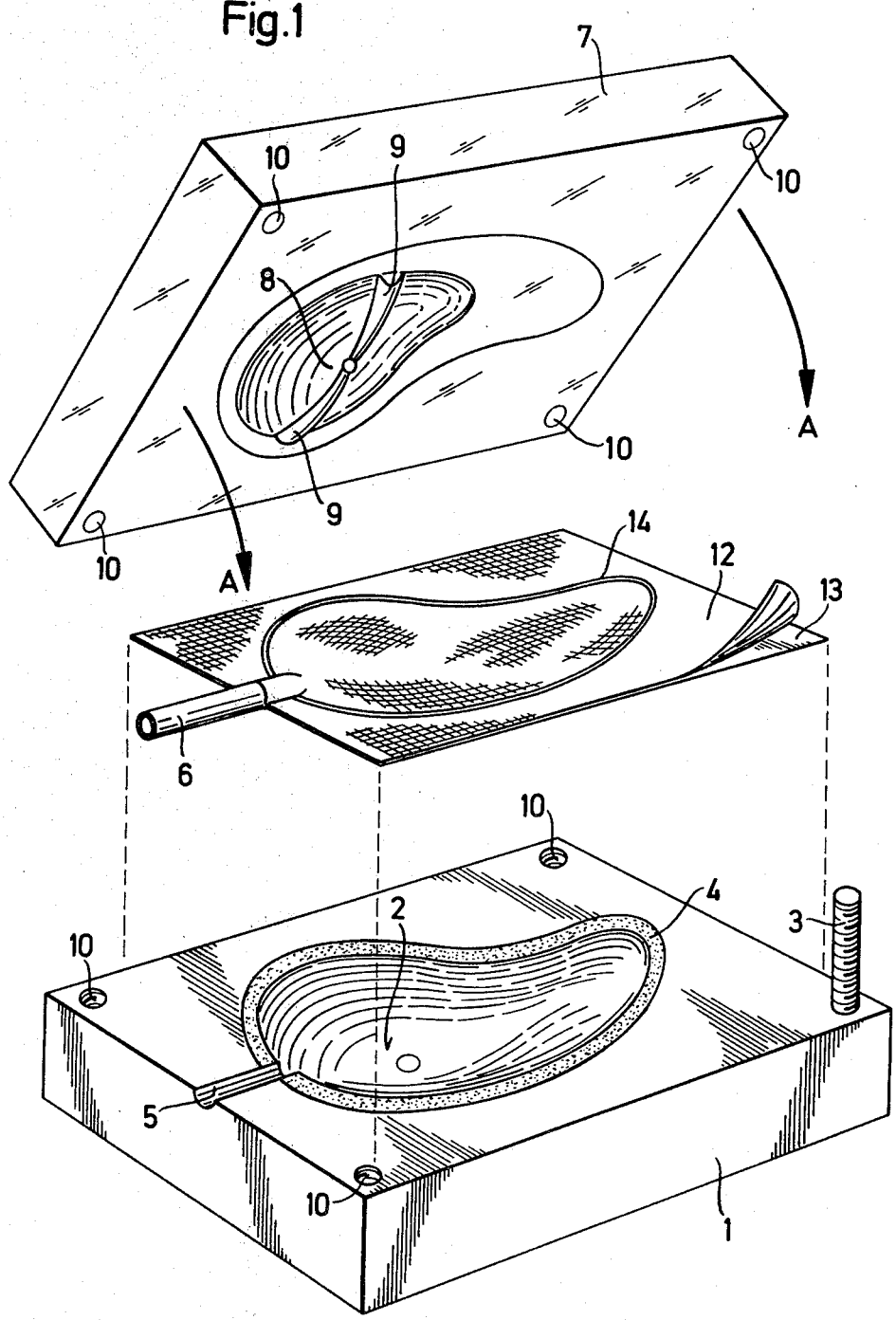

United States Patent [19]

Rechenberg

[11] 4,249,975
[45] Feb. 10, 1981

[54] PROCESS OF MANUFACTURING ARTIFICIAL BREASTS

[76] Inventor: Cornelius Rechenberg, Weidach 22, 8204 Brannenburg, Fed. Rep. of Germany

[21] Appl. No.: 40,636

[22] Filed: May 21, 1979

Related U.S. Application Data

[63] Continuation-in-part of Ser. No. 933,168, Aug. 14, 1978, abandoned.

[51] Int. Cl.³ .................. B29C 19/00; A41C 3/10; B29C 23/00; B29H 9/00
[52] U.S. Cl. ........................... 156/245; 264/46.6; 264/46.8; 264/267; 3/36
[58] Field of Search .............. 156/245, 251; 264/46.6, 264/46.8, 222, 266, 267, DIG. 34; 3/36; 128/463

[56] References Cited

U.S. PATENT DOCUMENTS

| | | | |
|---|---|---|---|
| 2,962,767 | 12/1960 | Trojanowski | 264/DIG. 34 |
| 3,048,169 | 8/1962 | Pierce | 264/222 |
| 3,230,663 | 1/1966 | Shabram | 156/251 |
| 4,116,736 | 9/1978 | Sanson et al. | 264/46.6 |

FOREIGN PATENT DOCUMENTS

2605148  11/1977  Fed. Rep. of Germany.

Primary Examiner—John T. Goolkasian
Assistant Examiner—L. Falasco
Attorney, Agent, or Firm—Howard C. Miskin

[57] ABSTRACT

A process for manufacturing artificial breasts uses a two-component silicone rubber composition capable of a cross linking addition reaction, has cups sheathed by plastic sheeting layers initially joined by welding except for one opening through which the silicone composition is introduced under pressure and then the composition is vulcanized and the opening closed by welding.

4 Claims, 2 Drawing Figures

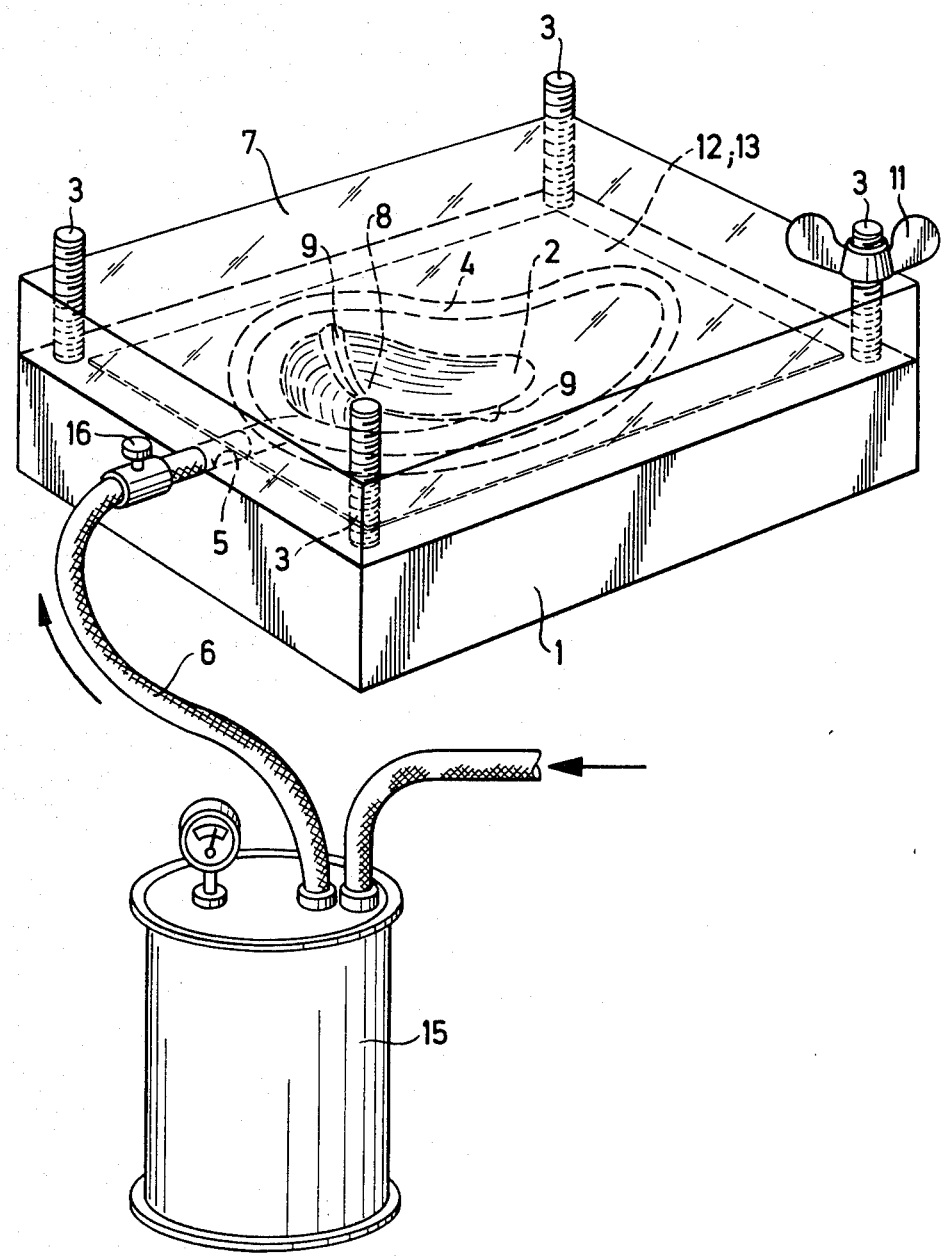

PROCESS OF MANUFACTURING ARTIFICIAL BREASTS

This application is a continuation-in-part of my copending application Ser. No. 933,168 filed Aug. 14, 1978 now abandoned.

This invention relates to a process of manufacturing an artificial breast consisting of a shell-like body which is similar in shape to the breast and consists of an addition cross-linking two-component silicone rubber composition and is enclosed in plastic material sheeting layers joined by welding, in which process a sheath of the artificial breast is formed in that two flat layers of plastic material sheeting are joined by welding, except for a filling opening, along an edge which is to form the edge of the artificial breast, and said layers are fixed adjacent to the welded edge to the edge of a lower mold part of a two-part mold, which has an internal cavity that conforms to the contour of the artificial breast, according to German Pat. (DE) No. 27 01 627.

In accordance with the main patent, the layers of plastic material sheeting which have been joined by welding to form a sheath are laid into the lower mold part, the latter is then closed by an upper mold part and the two-component silicone rubber composition is subsequently charged under pressure through the charging opening in the welded edge into the sheath of plastic material until the composition charged into the sheath has forced the walls of the sheath against the boundary surfaces of the mold cavity. When the composition has been charged into the sheath gripped in the mold, it may be necessary to check whether the two-component silicone rubber composition has been charged without bubbles because any bubbles must be collected at the charging opening and permitted to escape in that the charging opening is temporarily opened. In practice, the check for bubbles is enabled in that the upper mold part is provided in the form of a cover, which can be opened as often as desired when the mold has been charged and before it is pushed into the oven, in which the mold and its contents are heated to accelerate the curing of the composition. This opening of the cover will not change the position of the sheath formed by the layers of plastic material sheeting joined by welding because the welded edge of the sheath is fixed to the lower mold part at the edge of the cavity which corresponds to the shape of the breast. This fixation may be accomplished in that the edge of the sheath if clamped to the lower mold part.

Before the vulcanizing treatment, it is not necessary at all to place the upper part of the mold on its lower part so as to close the mold only in order to ensure that the two-component silicone rubber composition is introduced through the charging opening into the sheath in a quantity which corresponds to the volume of the mold cavity. If the volume of the mold cavity is known, the composition can be charged into the sheath in a quantity which corresponds to that volume when the upper part of the mold has been removed. In this case the charging operation can be watched so that any air bubbles can be detected. For this reason the upper part of the mold need not be applied to close the mold until any air bubbles have been removed before the mold is subjected to the vulcanizing treatment.

In accordance with the present invention the process according to the main patent is improved in that the two-component silicone rubber composition is charged in a quantity which corresponds to the volume of the mold cavity through the charging opening left in the welded edge into the sheath formed by the layers of plastic material sheeting and the lower mold part is not finally closed by the upper mold part until the composition is about to be subjected to the vulcanizing treatment in the mold. Because the composition is charged into the still open mold in an exactly controlled quantity, which corresponds to the volume of the mold cavity, the composition which is enclosed in the sheath is caused to assume the shape of the mold cavity when the upper part of the mold is applied. That upper part of the mold defines the rear hollow of the artificial breast.

Any air bubbles which have formed in the sheath as the composition has been charged can be collected at the charging opening and the latter can be opened to permit said bubbles to escape. The charging opening is suitably defined by a flexible tube, which extends through a non-welded portion of the edge. Such flexible tube can be closed simply by squeezing.

The charging of the two-component silicone rubber composition in a quantity which corresponds to the volume of the mold cavity into the sheath formed by the welded sheeting layers is suitably effected by two separately controlled pumps, which supply respective components of the composition.

The charging opening left in the welded edge of the sheath is suitably welded under the action of the vulcanizing heat. For this purpose, a punch may be provided in the mold and may be forced during the vulcanizing treatment against the non-welded edge portion which defines the charging opening.

The upper mold part which closes the mold is suitably resiliently held in its holder so that the cover can be slightly raised during the vulcanizing treatment when the composition which undergoes vulcanization expands slightly as it is heated.

In the oven in which the mold is placed to cure the composition, the air for heating the mold is suitably circulated. This circulation of the air for heating the mold results in a uniform distribution of temperature in the oven so that certain temperature limits are not exceeded and an excessive expansion of the silicone rubber so as to overstretch the enclosing sheath is prevented. Such overstretching would subsequently result in a formation of wrinkles in the sheeting so that a smooth finished product cannot be obtained.

An illustrative embodiment of the invention will now be described more fully with reference to the drawing, in which FIG. 1 is a perspective view showing the mold in an open state and FIG. 2 is a perspective view showing the mold in a closed state and the container which is connected by a flexible tubing and contains the mixed components of a silicone rubber capable of a cross-linking addition reaction.

The base part 1 of the mold is formed with a cavity 2, which corresponds to the shape of the breast. The base part 1 has the shape of a rectangular parallele-piped and in the corner portions of this flat top surface is provided with four vertical threaded studs 3, only one of which is shown. A tape 4 which is coated with adhesive on both sides is placed on the top surface of the mold part 1 at the edge portion surrounding the cavity 2. The mold part 1 is also formed with a groove 5, which leads into the cavity 2 and has the same cross-section as the flexible supply tubing 6 through which the silicone rubber composition is charged into the mold.

The mold cover 7 consists of a rectangular slab having an adequate resistance to heat. On that side which faces the cavity 2, the cover 7 is formed with an elevation 8 which conforms to the cavity on the rear of the artificial breast and is resiliently held so that it can be slightly raised. The elevation 8 is formed with beads 9 extending across the elevation. These beads cause ventilation grooves to be formed in the rear surface of the artificial breast.

The cover 7 has four bores 10, which are aligned with the studs 3. When it is desired to close the mold, the cover 7 is pivotally moved in the direction of arrows A to receive the studs 3 and is then fixed to the mold base in that wing nuts 11 shown in FIG. 2 are screwed on the studs 3.

When it is desired to manufacture an artificial breast, two flat-lying sheeting layers 12, 13 of polyurethane are joined by a peripheral seam weld 14, which has approximately the same configuration as the edge of the cavity 2 in the mold part 1. This is shown in FIG. 1. An opening is left in the welded edge 14 so that the flexible tubing 6 can be introduced between the sheeting layers through that opening. When the sheeting layers have thus been prepared, they are placed on the mold base 1, the welded edge 14 is secured to the adhesive tape 4, which surrounds the cavity 2, and the flexible tubing 6 is placed into the groove 5.

Before the cover 7 has been placed on the mold base 1, a predetermined quantity of the silicone rubber composition is charged under pressure through the flexible tubing 6 between the sheeting layers 12, 13 in the mold cavity to expand the sheath defined by the welded layers 12, 13 and any included gas bubbles are removed in the manner explained above.

The mold is then closed and the filled mold is then placed in a heating cabinet, in which the silicon rubber composition is caused to cross-link at temperatures between 100° and 150° C. for one to two hours.

When it is desired to charge the mold, the mixed components of the silicone rubber composition which is capable of a cross-linking addition reaction are placed in a container 15, which is then closed and pressurized with air under a pressure of about 2 bars. The flexible tubing 6 is air-tightly fitted through the cover of the container 15 and extends below the surface of the liquid silicone rubber composition so that a predetermined fixed quantity of the latter flows under pressure into the mold when the valve 16 is opened.

The resulting silicone elastomers are of the RTV (room temperature vulcanizing) type and are produced from organopolysiloxanes which contain alkenyl and Si—H bonds by vulcanization at elevated temperature in the presence of noble metal catalysts, such as platinum and platinum compounds. Pure elastomers or elastomers containing organosiloxane resin are thus formed, depending on the kind and number of the functional groups in the organopolysiloxanes which contain Si—H bonds. Whereas the linear organopolysiloxanes can be vulcanized at room or body temperature in the presence of noble metal catalysis, it is preferable to vulcanize them at slightly elevated temperature. The vulcanizing time of the mixture in the presence of a catalyst is 1 to 6 hours at 40° to 120° C.

The two-component silicone rubber compositions which are capable of a cross-linking addition reaction which are used within the scope of the invention have been described more fully in "Chemiker-Zeitung," 97th Year, 1973, No. 4, on pages 176–180). They are sold by Wacker-Chemie-GmbH under the type designations SLM 71158-3 (component A) and SLM 71159-3 (component B).

I claim:

1. A process of manufacturing an artificial breast consisting of a shell-like body which is similar in shape to the breast and consists of an addition cross-linking two-component silicone rubber composition and is enclosed in plastic material sheeting layers joined by welding, in which process a sheath of the artificial breast is formed by welding two flat layers of plastic material sheeting, except for a filling opening, along an edge which is to form the edge of the artificial breast, said layers are releasably fixed adjacent to the welded edge to the edge of the cavity in an open lower mold part of a two-part mold, of a breast which has an internal cavity that conforms to the contour of the artificial breast, the two-component silicone rubber composition is charged in a predetermined quantity which corresponds to the volume of the mold cavity through the charging opening left in the welded edge into the sheath formed by the layers of plastic material sheeting while the lower mold part is at least partially open to provide to the charged sheath and thereafter the lower mold part is finally closed by the upper mold part and the composition is subjected to the vulcanizing treatment in the mold.

2. A process according to claim 1, characterized in that the charging of the two-component silicone rubber composition in a quantity which corresponds to the volume of the mold cavity into the sheath formed by the welded sheeting layers is effected by two separately controlled pumps, which supply respective components of the composition.

3. A process according to claim 1, characterized in that the charging opening left in the welded edge is welded by the vulcanizing heat.

4. A process according to claim 1, characterized in that the air for heating the mold is circulated in the oven in which the mold is placed to cure the composition.

* * * * *

UNITED STATES PATENT OFFICE
CERTIFICATE OF CORRECTION

PATENT NO. : 4,249,975
DATED : February 10, 1981
INVENTOR(S) : Cornelius Rechenberg It is certified that error appears in the above–identified patent and that said Letters Patent are hereby corrected as shown below:

In Claim 1, at column 4, line 38, after "provide" insert --access--.

Signed and Sealed this

Twenty-sixth Day of March 1985

[SEAL]

Attest:

DONALD J. QUIGG

Attesting Officer      Acting Commissioner of Patents and Trademarks

REEXAMINATION CERTIFICATE (835th)
United States Patent
[11] B1 4,249,975

Rechenberg

[45] Certificate Issued  Apr. 5, 1988

[54] PROCESS OF MANUFACTURING ARTIFICIAL BREASTS

[75] Inventor: Cornelius Rechenberg, Brannenburg, Fed. Rep. of Germany

[73] Assignee: Amoena Corp., Atlanta, Ga.

Reexamination Request:
No. 90/001,239, May 11, 1987

Reexamination Certificate for:
Patent No.: 4,249,975
Issued: Feb. 10, 1981
Appl. No.: 40,636
Filed: May 21, 1979

Certificate of Correction issued Mar. 26, 1985.

Related U.S. Application Data

[63] Continuation-in-part of Ser. No. 933,168, Aug. 14, 1978, abandoned.

[51] Int. Cl.⁴ .................. B29C 45/16; A41C 3/14; B29C 51/44
[52] U.S. Cl. .................. 156/245; 264/46.6; 264/46.8; 264/267; 623/7
[58] Field of Search .............. 128/463; 156/245, 251; 264/46.6, 46.8, 222, 261, 266, 267, DIG. 34; 623/7, 8

[56] References Cited

U.S. PATENT DOCUMENTS

| | | | |
|---|---|---|---|
| 4,172,298 | 10/1979 | Rechenberg | 623/7 |
| 4,356,573 | 11/1982 | Knoche | 623/7 |
| 4,426,742 | 1/1984 | Prahl | 623/7 |

FOREIGN PATENT DOCUMENTS 2094092  2/1972  France.

*Primary Examiner*—Robert A. Dawson

[57] ABSTRACT

A process for manufacturing artificial breasts uses a two-component silicone rubber composition capable of a cross linking addition reaction, has cups sheathed by plastic sheeting layers initially joined by welding except for one opening through which the silicone composition is introduced under pressure and then the composition is vulcanized and the opening closed by welding.

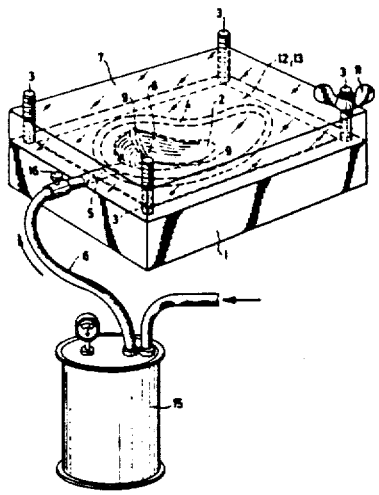

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1-4 is confirmed.

* * * * *